United States Patent
Gluchowski

Patent Number: 5,112,822
Date of Patent: * May 12, 1992

[54] (2-IMIDAZOLIN-2-YLAMINO) QUINOXALINE DERIVATIVES AND METHODS FOR USING SAME

[75] Inventor: Charles Gluchowski, Mission Viejo, Calif.

[73] Assignee: Allergan, Inc., Irvine, Calif.

[*] Notice: The portion of the term of this patent subsequent to Dec. 31, 2008 has been disclaimed.

[21] Appl. No.: 560,776

[22] Filed: Jul. 31, 1990

Related U.S. Application Data

[63] Continuation-in-part of Ser. No. 420,817, Oct. 12, 1989, Pat. No. 5,077,292.

[51] Int. Cl.$^5$ .................. A61K 31/495; C07D 403/10
[52] U.S. Cl. ..................... 514/249; 544/353; 544/354; 548/351
[58] Field of Search .............. 514/249; 544/353, 354

[56] References Cited

U.S. PATENT DOCUMENTS 3,890,319  6/1975  Danielewicz et al. .............. 544/353
5,021,416  6/1991  Gluchowski ...................... 514/249

FOREIGN PATENT DOCUMENTS 2538620  3/1976  Fed. Rep. of Germany

OTHER PUBLICATIONS

Fielding, "Clonidine:New Research in Psychotropic Drug Pharmacology, Medicinal Research Reviews", vol. 1, No. 1 pp. 97-123 (1981).
Isom et al., "a2-Adrenergic Receptors Accelerate Na/H Exchange in Neuroblastoma X Glioma Cells", The Journal of Biological Chemistry, vol. 262, No. 14, issue of May 15, 1987, pp. 6750-6757.
Pieter et al., "Clonidine and Some Bridge Analogues; Cardiovascular Effects and Nuclear Magnetic Resonance Data ($^1$H/$^{13}$)", Eur. J. Med. Chem, Jul.-Aug. 1980, vol. 4, pp. 323-329.
Jumblatt et al., "Alpha-2 Adrenergic Modulation of Norepinephrine Secretion in the Perfused Rabbit Iris-Ciliary Body", Current Eye Research, 1987, vol. 6, pp. 767-777.
Burke et al., "Ocular Effects of a Relatively Selective a2 Agonist (UK-14, 304-18) in Cats, Rabbits and Monkeys", Current Eye Research, 1986, vol. 5, pp. 665-676.
Fondacaro et al., "Selective Alpha-2 Adrenoceptor Agonists Alter Fluid and Electrolyte Transport in Mammalian Small Intestine American Society for Pharmacology", vol. 247, p. 481 (1988).
Gellai et al., "Mechanism of a2-Adrenoceptor Agonist-Induced Diuresis American Physiological Society 1988".
Dharmsathaphorn, a2-Adrenergic Agonists: A Newer Class of Antidiarrheal Drug Gastroenterology 1986, vol. 91, pp. 769-775.
Mittag. "Ocular Effects of Selective Alpha-Adrenergic Agents: A New Drug Paradox", Annals of Ophthalmology Mar. 1983, p. 201.
Gellai et al., "Renal Effects of Selective Alpha-1 and Alpha-2 Adrenoceptor Agonists in Conscious Normotensive Rats", The Journal of Pharmacology, vol. 240, p. 723 (1987).
Jarrot, "Clonidine and Related Compounds", Handbook of Hypertension, vol. 5, p. 113 (1984).

*Primary Examiner*—John M. Ford
*Assistant Examiner*—E. Bernhardt
*Attorney, Agent, or Firm*—Frank J. Uxa, Jr.; Gordon L. Peterson

[57] ABSTRACT

A compound selected from the group consisting of those having the formula:

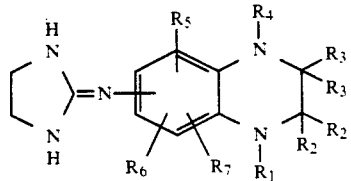

and pharmaceutically acceptable acid addition salts thereof, wherein $R_1$ and $R_4$ are independently selected from the group consisting of H and alkyl radicals having 1 to 4 carbon atoms; the $R_2$s are each H or alkyl radicals having 1 to 4 carbon atoms or are, together, oxo; the $R_3$s are each H or alkyl radicals having 1 to 4 carbon atoms or are, together, oxo, provided that the $R_2$s or the $R_3$s are alkyl radicals; the 2-imidazolin-2-ylamino group may be in any of the 5-, 6-, 7- or 8-positions of the quinoxaline nucleus; and $R_5$, $R_6$ and $R_7$ each is located in one of the remaining 5-, 6-, 7- or 8-positions of the quinoxaline nucleus and is independently selected from the group consisting of Cl, Br, H and alkyl radicals having 1 to 3 carbon atoms. Such compounds, when administered to a mammal, provide desired therapeutic effects, such as alteration in the rate of fluid transport in the gastrointestinal tract, reduction in intraocular pressure, and increase in renal fluid flow.

37 Claims, No Drawings

(2-IMIDAZOLIN-2-YLAMINO) QUINOXALINE DERIVATIVES AND METHODS FOR USING SAME

RELATED APPLICATION

This application is a continuation-in-part of co-pending patent application Ser. No. 420,817, filed Oct. 12, 1989, now U.S. Pat. No. 5,077,292.

BACKGROUND OF THE INVENTION

The present invention relates to novel substituted derivatives of quinoxaline. More particularly, the invention relates to such derivatives which are useful as therapeutic agents, for example, to effect reduction in intraocular pressure, to increase renal fluid flow and to effect an alteration in the rate of fluid transport in the gastrointestinal tract.

Various quinoxaline derivatives have been suggested as therapeutic agents. For example, Danielewicz, et al U.S. Pat. No. 3,890,319 discloses compounds as regulators of the cardiovascular system which have the following formula:

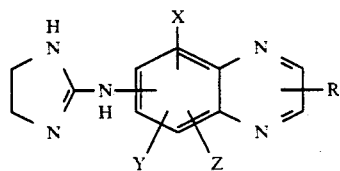

where the 2-imidazolin-2-ylamino group may be in any of the 5-, 6-, 7- or 8- position of the quinoxaline nucleus; X, Y and Z may be in any of the remaining 5-, 6-, 7-, 8- positions and may be selected from hydrogen, halogen, lower alkyl, lower alkoxy or triflucromethyl; and R is an optional substituent in either the 2- or 3- position of the quinoxaline nucleus and may be hydrogen, lower alkyl or lower alkoxy.

SUMMARY OF THE INVENTION

The novel compounds of the present invention are those having the formula:

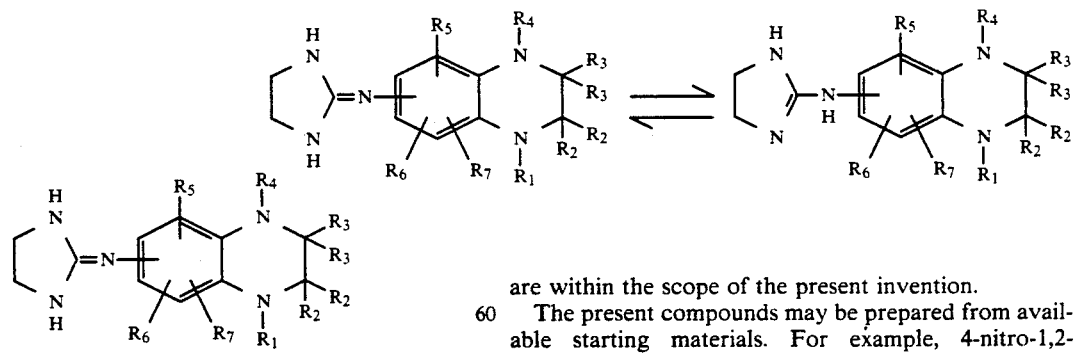

and pharmaceutically acceptable acid addition salts thereof, wherein $R_1$ and $R_4$ are independently selected from the group consisting of H and alkyl radicals having 1 to 4 carbon atoms; the $R_2$s are each H or alkyl radicals having 1 to 4 carbon atoms or are, together, oxo; the $R_3$s are each H or alkyl radicals having 1 to 4 carbon atoms or are, together, oxo, provided that the $R_2$s or the $R_3$s are alkyl radicals; the 2-imidazolin-2-ylamino group may be in any of the 5-, 6-, 7- or 8- positions of the quinoxaline nucleus; and $R_5$, $R_6$ and $R_7$ each is located in one of the remaining 5-, 6-, 7- or 8- positions of the quinoxaline nucleus and is independently selected from the group consisting of Cl, Br, H and alkyl radicals having 1 to 3 carbon atoms.

Particularly useful compounds are those in which $R_1$ and $R_4$ are H, the 2-imidazolin-2-ylamino group is in the 6-position of the quinoxaline nucleus, $R_5$ is selected from the group consisting of Cl, Br and alkyl radicals containing 1 to 3 carbon atoms, more preferably Br, and is in the 5- position of the quinoxaline nucleus, and $R_6$ and $R_7$ are H.

In one embodiment, the $R_2$s or $R_3$s are methyl radicals. The other of the $R_2$s or $R_3$s, i.e., those that are not alkyl, e.g., methyl, radicals, are H, or together is oxo.

Pharmaceutically acceptable acid addition salts of the compounds of the invention are those formed from acids which form non-toxic addition salts containing pharmaceutically acceptable anions, such as the hydrochloride, hydrobromide, hydroiodide, sulphate or bisulfate, phosphate or acid phosphate, acetate, maleate, fumarate, oxalate, lactate, tartrate, citrate, gluconate, saccharate and p-toluene sulphonate salts.

The present compounds provide one or more therapeutic effects, e.g., in mammals. Thus, these compounds are useful in a method for treating a mammal in which one or more of these compounds are administered to a mammal in an amount sufficient to provide the desired therapeutic effect in the mammal. Among the desired therapeutic effects provided by the present compounds include altering the rate of fluid transport in the gastrointestinal tract of a mammal; reducing or maintaining the intraocular pressure in at least one eye of a mammal; and increasing the renal fluid flow in at least one kidney of a mammal.

DETAILED DESCRIPTION OF THE INVENTION

The compounds of the present invention, are as described above. All stereoisomers, tautomers and mixtures thereof which comply with the constraints of one or more formulae of the present compounds are included within the scope of the present invention. For example, both tautomers are within the scope of the present invention.

The present compounds may be prepared from available starting materials. For example, 4-nitro-1,2-phenylenediamine may be reacted with an appropriate halide substituted carbonyl halide, in particular, a bromide substituted carbonyl bromide. This reaction, which provides for substitution of one of the amine groups on the phenylene ring by the carbonyl halide, is preferably conducted in a solvent and preferably at a temperature in the range of about 10° C. to about 50° C., in particular about room temperature. Reaction pressure is preferably such that the solvent is maintained substantially in the liquid phase. The reaction preferably occurs over a period of time in the range of about 2 hours to about 24 hours. Examples of useful solvents include methylene chloride ($CH_2Cl_2$), chloroform ($CHCl_3$), tetrahydrofuran and the like. A trialkyl amine, e.g., triethylamine, may be used as part of the solvent and/or to promote or facilitate the substitution reaction.

The resulting mixture of halo amide isomers are recovered preferably by conventional techniques, e.g., extraction, washing, drying, concentration, chromatography and the like, from the substitution reaction mixture. The isomers are then cyclized. This cyclization is preferably effected at a temperature in the range of about 10° C. to about 50° C., in particular at room temperature, by contacting the isomers, preferably dissolved in a solvent such as methylene chloride, with a cyclizing agent, such as $AgBF_4$, $AgNO_3$ and the like. Reaction pressure is preferably such that the solvent is maintained substantially in the liquid phase. The reaction preferably occurs over a period of time in the range of about 1 hour to about 24 hours. Conventional techniques, e.g., such as noted above, can be used to recover the cyclized isomers. Chromography can be used to separate the isomers and provide them in substantially pure form.

The cyclized compound produced as described above, identified as a nitro-substituted quinoxalinone, is hydrogenated to convert the nitro group to an amino group. This hydrogenation preferably occurs with the nitro-substituted quinoxalinone dissolved in a liquid, e.g., a lower alcohol such as methanol, ethanol or the like. A catalyst effective to promote the hydrogenation is preferably present. Examples of such catalysts include the platinum group metals, in particular palladium, platinum group metal compounds, such as platinum oxide, and mixtures thereof. Hydrogen, e.g., free molecular hydrogen, is present in an amount at least sufficient to provide the desired hydrogenation, preferably in an amount in excess of that required to provide the desired hydrogenation. The temperature and pressure at which the hydrogenation occurs are preferably selected to maintain the nitro-substituted quinoxalinone and hydrogenated product substantially in the liquid phase. Temperatures in the range of about 10° C. to about 100° C. and pressures in the range of about 0.5 atmospheres to about 5 atmospheres often provide acceptable results. These conditions are maintained for a time sufficient to provide the desired hydrogenation reaction. This period of time is often in the range of about 1 hour to about 16 hours. The hydrogenated product is separated from the hydrogenation reaction mixture and recovered, e.g., using conventional techniques.

At this point, the hydrogenated product may be subjected to one or more reactions to include one or more groups in the compound, as desired. For example, in one embodiment, it is preferred that the final quinoxaline derivative of the present invention includes at least one halide group, in particular a bromo group, on the aromatic ring structure. In order to provide such a bromo group, the above-noted hydrogenated product is brominated. Such bromination can occur by dissolving the hydrogenated product in a suitable solvent, e.g., glacial acetic acid, trifluoroacetic acid and the like, and contacting this solution with bromine. The mixture is preferably maintained at a suitably low temperature, e.g., in the range of about 10° C. to about 50° C., so that the degree of bromination can be controlled. Cooling or removing heat from the reaction mixture may be desirable. Room temperature bromination provides satisfactory results. Reaction pressure is preferably such that the solvent is maintained substantially in the liquid phase. The reaction preferably occurs over a period of time in the range of about −0.25 hours to about 6 hours. Conventional techniques, e.g., vacuum filtration, can be used to recover the brominated product, which may be a hydrobromide salt.

The above-noted hydrogenated product or substituted hydrogenated product is reacted with 2-imidazoline-2-sulfonic acid to produce a 2-imidazolin-2-ylamino quinoxaline derivative of the present invention. Such derivatives include an oxo group. This reaction can occur by dissolving the reactants in an appropriate solvent, e.g., an alcohol such as isobutanol, and heating this solution to reflux at atmospheric pressure. Preferred reaction temperatures are in the range of about 70° C. to about 150° C. Reaction pressure is preferably such that the solvent is refluxed or maintained substantially in the liquid phase. The reaction preferably occurs over a period of time in the range of about 1 hour to about 24 hours. Conventional techniques, e.g., concentration and chromatography, can be used to recover the desired quinoxaline derivative.

The present quinoxaline derivatives which do not include an oxo group can be obtained by reacting the above-described oxo-containing quinoxaline derivatives to remove the oxo group. This can be accomplished by dissolving the oxo containing material in an appropriate solvent, e.g., tetrahydrofuran, acetic acid, trifluoroacetic acid, diethyl ether and the like, and subjecting this solution to a hydride reducing agent, such as $LiAlH_4$, $NaBH_4$, $NaCNBH_3$ and the like. Reaction temperatures in the range of about 20° C. to about 100° C. can be used. Conventional techniques, e.g., cooling, concentration and chromatography, can be employed to provide the present quinoxaline derivative which do not include an oxo group.

For compounds in which $R_1$ and/or $R_4$ are to be alkyl, the quinoxaline derivative (having no substituents corresponding to $R_1$ and $R_4$) may be reacted with a suitable hydride reducing agent in the presence of a selected aldehyde or aldehydes. The aldehyde or aldehydes used are selected based on the specific $R_1$ and/or $R_4$ alkyl group or groups desired. For example, if $R_1$ and/or $R_4$ is to be methyl, formaldehyde is used, if $R_1$ and/or $R_4$ is to be ethyl, acetaldehyde is used, etc. The temperature and pressures at which the reaction occurs are preferably selected to maintain the quinoxaline derivative and product in the liquid phase. Temperatures in the range of about 0° C. to about 50° C. and pressure in the range of about 0.5 atmospheres to about 2 atmospheres often provide acceptable results. The reaction time is often in the range of about 1 hour to about 24 hours. The amount of aldehyde used may vary depending on the final compound desired. A mixture of final compounds, i.e., a compound in which both $R_1$ and $R_4$ are alkyl mixed with compounds in which only one of $R_1$ or $R_4$ is alkyl, may be produced by the reaction. One or more individual quinoxaline derivatives of the present invention can be separated and recovered from this mixture, e.g., using conventional techniques.

The present compounds are useful to provide one or more desired therapeutic effects in a mammal. Among the desired therapeutic effects are an alteration, preferably a decrease, in the rate of fluid transport in the gastrointestinal tract of a mammal, a reduction in or maintenance of the intraocular pressure in at least one eye of a mammal; and an increase in the renal fluid flow in at least one kidney of a mammal. Thus, for example, the present compounds may be effective as an anti-diarrhea agent, a medication for use in the treatment or management of glaucoma, and/or a medication for use in the treatment or management of kidney disease. One important feature of many of the present compounds is that the desired therapeutic effect is achieved with reduced side effects, in particular with reduced effects on the blood pressure of the mammal to which the present compound is administered.

Any suitable method of administering the present compound or compounds to the mammal to be treated may be used. The particular method of administration chosen is preferably one which allows the present compound or compounds to have the desired therapeutic effect in an effective manner, e.g., low medication concentration and low incidence of side effects. In many applications, the present compound or compounds are administered to a mammal in a manner substantially similar to that used to administer alpha agonists, in particular alpha 2 agonists, to obtain the same or a similar therapeutic effect.

The present compound or compounds may be included in a medication composition together with one or more other components to provide a medication composition which can be effectively administered. Such other components, e.g., carriers, anti-oxidants, bulking agents and the like, may be chosen from those materials which are conventional and well known in the art, e.g., as being included in medication compositions with alpha 2 agonists.

The present compounds are often administered to the eye of a mammal to reduce or maintain intraocular pressure in the form of a mixture with an ophthalmically acceptable carrier. Any suitable, e.g., conventional, ophthalmically acceptable carrier may be employed. Such a carrier is ophthalmically acceptable if it has substantially no long term or permanent detrimental effect on the eye to which it is administered. Examples of ophthalmically acceptable carriers include water, in particular distilled water, saline and the like aqueous media. The present compounds are preferably administered to the eye as a liquid mixture with the carrier. The compounds are more preferably soluble in the carrier so that the compounds are administered to the eye in the form of a solution.

When an ophthalmically acceptable carrier is employed, it is preferred that the mixture contain one or more of the present compounds in an amount in the range of about 0.0001% to about 1%, more preferably about 0.05% to about 0.5%, W/V.

Any method of administering drugs directly to a mammalian eye may be employed to provide the present compound or compounds to the eye to be treated. By the term "administering directly" it is meant to exclude those general systemic drug administration modes, e.g., injection directly into the patients blood vessels, oral administration and the like, which result in the compound or compounds being systemically available. The primary effect on the mammal resulting from the direct administering of the present compound or compounds to the mammal's eye is preferably a reduction in intraocular pressure. More preferably, the present compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer systemic side effects. An exemplary topical ophthalmic formulation is shown below in Table I. The abbreviation q.s. means a quantity sufficient to effect the result or to make volume.

TABLE I

| Ingredient | Amount (% W/V) |
|---|---|
| Present Quinoxaline Derivative | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| Antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetycysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The following non-limiting examples illustrate certain aspects of the present invention.

EXAMPLE 1

Preparation of
1,2-dihydro-2,2-dimethyl-6-nitro-3-(4H)-quinoxalinone
and
3,4-dihydro-3,3-dimethyl-6-nitro-2-(1H)-quinoxalinone To a stirred solution of 4-nitro-1,2-phenylenediamine (Aldrich, 5.0 g, 32.6 mmol) and triethylamine (5.05 g, 50 mmol) in $CH_2Cl_2$ (50 ml) is added 2-bromo-2-methyl propionyl bromide (Aldrich 7.49 g, 32.6 mmol) dropwise. The mixture is stirred at room temperature until the starting material (4-nitro-1,2-phenylenediamine) is consumed. The reaction is quenched with aqueous $NH_4Cl$ and the organic material is extracted with CH$_2$Cl$_2$. The organic extract is washed with H$_2$O (20 ml), dried over MgSO$_4$ and concentrated in vacuo. The residue is chromatographed on silica gel with hexanes: ethyl acetate elution to yield a mixture of bromo amide isomers. This mixture is dissolved in CH$_2$Cl$_2$ (30 ml) and treated with AgBF$_4$ (Aldrich, 6.36 g, 32.6 mmol) at room temperature to effect cyclization. After the starting bromo amide isomers are consumed, the reaction is quenched with aqueous NH$_4$Cl and the organic material is extracted with CH$_2$Cl$_2$. The organic extract is washed with H$_2$O (10 ml), dried over MgSO$_4$ and concentrated in vacuo. The residue is chromatographed on silica gel with hexanes: ethyl acetate elution to yield the title compounds in pure form. This chromatographing separates the title compounds and allows recovery of each of them individually.

EXAMPLE 2

Synthesis of 6-amino-1,2-dihydro-2,2-dimethyl-6-(2-imidazolin-2-ylamino)-3-(4H)-quinonxalinone A solution of 1,2-dihydro-2,2-dimethyl-6-nitro-3 (4H)-quinoxalinone(663 mg, 3 mmol) in CH$_3$OH (10 ml) is hydrogenated with 50 psi H2 (g) at room temperature in the presence of a catalyst of 10% by weight palladium on charcoal (50 mg). After the starting material is consumed, the solution is filtered and concentrated in vacuo to yield 6-amino-1,2- dihydro-2,2-dimethyl-3- (4H)-quinoxalinone.

EXAMPLE 3

Synthesis of 6-amino-5-bromo-1,2-dihydro-2,2-dimethyl-3-(4H)-quinoxalinone hydrobromide A solution of 6-amino-1,2-dihydro-2,2-dimethyl-3-(4H)-quinoxalinone (250 mg, 1.31 mmol) in glacial acetic acid (4 ml) is cooled using a water bath. Bromine (210 mg, 1.31 mmol) in acetic acid (0.25 ml) is added dropwise over a 5 minute period. The mixture is stirred at room temperature for 4 hours and the resulting precipitate is collected by vacuum filtration. The title compound is obtained in pure form after drying in vacuo.

EXAMPLE 4

Synthesis of 2-imidazoline-2-sulfonic acid

2-Imidazolidinethione (66.3 g, 650 mmol), Na$_2$MoO$_4$ (5 g, 227 mmol) and NaCl (15 g. 256 mmol) were added to 300 ml H$_2$O. Although some dissolution occurred, a solid residue remained in the liquid of the mixture. The mixture was <cooled to −10° C. using an immersion cooler. 500 ml of a 30% (w/v) aqueous H$_2$O$_2$ solution was placed in a jacketed controlled drip rate addition funnel and cooled to 0° C. using an ice/H$_2$O bath. The aqueous H$_2$O$_2$ solution was added to the mixture at a rate of 60 drops/minute. The mixture was stirred for 16 hours at −10° C. During this time, the mixture changed from a white suspension to a dark blue solution to a light blue suspension. At the end of 16 hours, a solid was filtered from the suspension and dried in vacuo. No further purification was needed. 57.8 g (a yield of 52.3%) of the title compound as a white solid, which was characterized spectroscopically, was recovered. This solid was stable when stored in the dark at ° C. for at least 6 months.

EXAMPLE 5

Synthesis of5-bromo-1,2dihydro-2,2-dimethyl-6-(2-imidazolin-2-ylamino)-3-(4H)-quinoxalinone A mixture of 6-amino-5-bromo-1,2-dihydro-2,2-dimethyl-3-(4H) - quinoxalinone hydrobromide (479 mg, 1 mmol) and 2-imidazoline-2-sulfonic acid (224 mg. 1.5 mmol) in isobutanol (5 ml) is heated at reflux until the starting hydrobromide material is consumed. The solvent is removed in vacuo and the residue chromatographed on silica gel with CHCl$_3$: CH$_3$OH saturated with NH$_3$(g) elution to yield the title compound.

EXAMPLE 6

Preparation of 5-bromo-2,2-dimethyl-6-(2-imidazolin-2-ylamino)-1,2,3,4-tetrahydroquinoxaline A suspension of 5-bromo-1,2-dihydro-2,2-dimethyl-6-(2-imidazolin-2-ylamino)-3-(4H)-quinoxali none (150 mg. 0.45 mmol) and LiALH$_4$ (17 mg, 0.45 mmol) in tetrahydrofuran (3 ml) is heated and maintained at a temperature of 50–80° C. until the starting material is consumed. The mixture is cooled to 0° C., 2–3 drops of H$_2$O is added and the mixture is filtered. The solution is concentrated in vacuo to yield a residue which is chromatographed on silica gel with CHCl$_3$: CH$_3$OH saturated with NH$_3$ (g) elution to produce the title compound.

EXAMPLE 7

Preparation of 5 bromo-3,4-dihydro-3,3-dimethyl-6-(2-imidazolin-2-ylamino)-2-(1H)-quinonxalinone By a series of reaction steps analogous to the steps described above in Examples 2 to 5, the title compound is prepared starting with 3,4-dihydro-3,3-dimethyl-6-nitro-2-(1H)-quinoxalinone in place of 1,2 dihydro-2,2-dimethyl-6-nitro-3-(4H)-quinoxalinone.

EXAMPLE 8

Preparation of 5-bromo-3,4-dihydro-3,3-dimethyl 6-(2-imidazolin-2-imidazolin-2-ylamino)-1,2,3,4-tetrahydro-quinoxaline Using the procedure illustrated in Example 6, the title compound is prepared starting with 5-bromo-3,4-dihydro 3,3-dimethyl-6-(2-imidazolin-2-ylamino)-2-(1H)-quinoxaline in place of 5-bromo-1,2-dihydro-2,2-dimethyl-6-(2-imidazolin-2-ylamino)-3-(4H)-quinoxalinone.

EXAMPLES 9 TO 12

The four (4) quinoxaline derivatives produced in accordance with Examples 5 to 8 are tested to determine what effect, if any, these materials have on intraocular pressure.

Each of these materials is dissolved in distilled water at a concentration of 0.1% (w/v). Each of these solutions is administered topically and unilaterally to one eye of a drug-naive, unanesthetized New Zealand white rabbit in a single 50 micro liter drop. The contralateral eye received an equal volume of saline prior to determining the intraocular pressure after the mixture is administered. Also, approximately 10 micro liters of 0.5% (w/v) proparacaine (topical anesthetic) is applied to the corneas of each of the rabbits before determining intraocular pressure. As a control test, six (6) other drug-naive, unanesthetized New Zealand white rabbits are treated and tested as described above except that no quinoxaline derivative is included in the solutions administered to the eyes.

The intraocular pressure is determined in both eyes of each rabbit before and after the solution is administered. Such intraocular pressure determinations are made in the conventional manner using conventional equipment.

Results of these IOP determinations indicate that the four (4) quinoxaline derivatives produced in Examples 5 to 8 are effective to reduce intraocular pressure in the treated rabbit eye, i.e., the eye to which the active material was directly administered.

EXAMPLES 13 TO 16

The quinoxaline derivatives produced in Examples 5 to 8 are tested for activity using the following in vitro methods.

Rabbit Vas Deferens: Alpha 2 Adrenergic Receptors

New Zealand white rabbits (2-3 kg) are killed by $CO_2$ inhalation and the vasa deferentia is removed. The prostatic ends of the vasa deferentia (2-3 cm lengths) are mounted between platinum ring electrodes in 9 ml organ baths and bathed in Krebs bicarbonate solution of the following composition (millimolar): NaCl 118.0; KCl 4.7; $CaCl_2$ 2.5; $MgSO_4$ 1.2; $KH_2PO_4$ 1.2; glucose 11.0; $NaHCO_3$ 25.0; which solution is maintained at 35° C. and bubbled with 95% $O_2$ and 5% $CO_2$. The initial tension of the vas deferens is 0.5 g. The tissues are left to equilibrate for 30 minutes before stimulation is started. Vasa are then field stimulated (0.1 Hz, 2 ms pulse width at 90 mA) using a square wave stimulator (WPI A310 Accupulser with A385 stimulus). The contractions of the tissue are recorded isometrically using Grass FTO3 force-displacement transducers and displayed on a Grass Model 7D polygraph. A cumulative concentration-response relationship is obtained for the quinoxaline derivative being tested with a 4 minute contact time at each concentration.

Each of the quinoxaline derivatives of Examples 5 to 8 is effective to reduce the response height. Therefore, such compounds may be properly classified as Alpha 2 agonists.

EXAMPLES 17 to 20

Each of the quinoxaline derivatives produced in Examples 5 to 8 is tested for renal and blood pressure effects using the following method.

Young male (20-24 weeks old) Sprague-Dawley rats are used. Under ketamine (60 mg/kg b.wt. i.m.) and pentobarbital (i.p. to effect) anesthesia, medical grade plastic tubes are implanted into the abdominal aorta and vena cava via the femoral vessels. In addition, a Silastic-covered stainless steel cannula is sewn in the urinary bladder. After the surgery, the rats are housed individually and are allowed free access to food and water until the day of the experiment.

For about 7 to 10 days before surgery and during recovery, the rats are accustomed to a restraining cage by placement in the cage for 2 to 3 hours every 2nd and 3rd day. The cage is designed for renal clearance studies (a model G Restrainer sold by Braintree Scientific, Inc., Braintree, MA). The animals' adjustment to the cage is judged by the stability of blood pressure and heart rate.

For an experiment, a rat is placed in the restraining cage, and the arterial line is connected to a Statham pressure transducer and a Beckman Dynograph R61 to monitor the mean arterial blood pressure, hereinafter referred to as MAP. The venous line is connected to an infusion pump system for infusion of replacement fluid. The quinoxaline derivative is administered intraduodenally by cannula. The bladder cannula was extended with a silastic tube to facilitate collection of urine in preweighed tubes. The volume of urine is measured gravimetrically. Body weight is recorded before and after the experiment.

Throughout the experiments, 0.9% NaCl containing 10% polyfructosan (Inutest) and 1% sodium PAH is infused at a rate of 20 microliters/min. An equilibration period of 60 minutes is followed by two consecutive 30 minute control clearance periods. Then, the quinoxaline derivative is administered for 90 minutes. Urine collection is resumed 10 minutes after the start of quinoxaline derivative administration. By this time the washout of the bladder cannula dead space (approximately 200 microliters) is completed. Three additional clearance measurements are made. Blood samples (150 microliters) are collected at the midpoint of urine collections. Plasma is separated and saved for analyses, and the cells are resuspended in saline and returned to the animals. Water and sodium loss is carefully replaced i.v. by a variable speed infusion pump.

Results of these tests indicate that the present quinoxaline derivatives produce renal effects, e.g., increased renal fluid flow. The effect on blood pressure of such derivatives is limited relative to such renal effects.

EXAMPLES 21 TO 24

Each of the quinoxaline derivative produced in Examples 5 to 8 is tested for anti-diarrheal effects and blood pressure effects using the following method.

Cecectomies are performed in unfasted rats in a conventional manner. The cecectomized rats are put into individual wire-bottomed cages placed over sheets of clean paper, and deprived of food and water for the duration of the assay. The MAP is monitored, as described in Examples 17 to 20, throughout the assay. Rats are given a 2 hour acclimatization period prior to the start of the assay in order to eliminate sporadic episodes of anxiety-induced defecation. During this period they are observed also for consistent occurrences of pelleted feces; an animal producing other than a pelleted stool is disqualified from the study.

Diarrhea is induced with oral administration of 16,16-dimethyl prostaglandin E2 ($dmPGE_2$) in 3.5% EtOH. The quinoxaline derivative is administered by gavage after the onset of diarrheal episodes. The cage papers are removed and examined at 30 minute intervals for $dmPGE_2$-induced diarrhea. Fecal output is recorded at each interval and fecal consistency is assigned a numerical score in each experimental group as follows: 1 = normal pelleted stool; 2 = soft-formed stools; 3 = water stool and/or diarrhea. The fecal output index (FOI) is defined as the summation of the number of defecation episodes and their ranked consistency score within an observation period.

Results of these tests indicate that the quinoxaline derivatives produced in Examples 5 to 8 provide substantial anti-diarrheal effects. Further, such anti-diarrheal effects are produced with no or relatively limited effects on blood pressure.

While this invention has been described with respect to various specific examples and embodiments, it is to be understood that the invention is not limited thereto and that it can be variously practiced within the scope of the following claims.

What is claimed is:

1. A compound selected from the group consisting of those having the formula

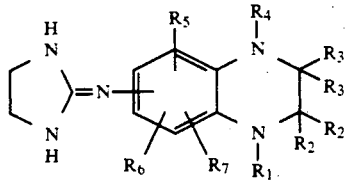

and pharmaceutically acceptable acid addition salts thereof, wherein $R_1$ and $R_4$ are independently selected from the group consisting of H and alkyl radicals having 1 to 4 carbon atoms; the $R_2$s are each H or alkyl radicals having 1 to 4 carbon atoms or are, together, oxo; the $R_3$s are each H or alkyl radicals having 1 to 4 carbon atoms or are, together, oxo, provided that said $R_2$s or said $R_3$s are alkyl radicals; the 2-imidazolin-2-ylamino group may be in any of the 5-, 6-, 7- or 8- positions of the quinoxaline nucleus; and $R_5$, $R_6$ and $R_7$ each is located in one of the remaining 5-, 6-, 7- or 8-positions of the quinoxaline nucleus and is independently selected from the group consisting of Cl, Br, H and alkyl radicals having 1 to 3 carbon atoms.

2. The compound of claim 1 wherein the 2-imidazolin-2-ylamino group is in the 6- position of the quinoxaline nucleus, $R_5$ is in the 5- position of the quinoxaline nucleus and is selected from the group consisting of Cl, Br and alkyl radicals containing 1 to 3 atoms and $R_6$ and $R_7$ are both H.

3. The compound of claim 2 wherein each of $R_1$ and $R_4$ is H.

4. The compound of claim 2 wherein said said $R_2$s or said $R_3$s are methyl radicals.

5. The compound of claim 3 wherein said $R_2$s or said $R_3$s are methyl radicals.

6. The compound of claim 2 wherein said $R_2$s or said $R_3$s are H.

7. The compound of claim 3 wherein said $R_2$s or said $R_3$s are H.

8. The compound of claim 2 wherein said $R_2$s or said $R_3$s together is oxo.

9. The compound of claim 3 wherein said $R_2$s or said $R_3$s together is oxo.

10. The compound of claim 2 wherein $R_5$ is Br.
11. The compound of claim 3 wherein $R_5$ is Br.
12. The compound of claim 4 wherein $R_5$ is Br.
13. The compound of claim 6 wherein $R_5$ is Br.
14. The compound of claim 8 wherein $R_5$ is Br.
15. The compound of claim 1 having the formula:

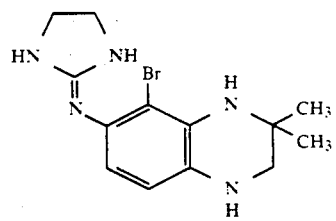

16. The compound of claim 1 having the formula:

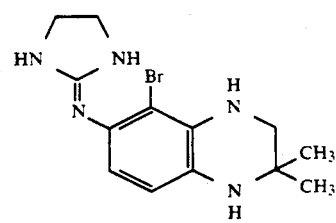

17. The compound of claim 1 having the formula:

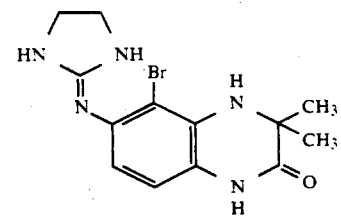

18. The compound of claim 1 having the formula:

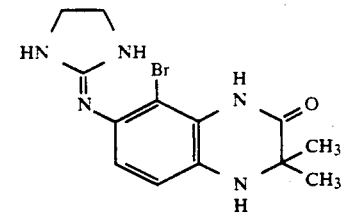

19. A medication composition comprising:
an amount of a compound effective to provide a desired therapeutic effect in a mammal to which said amount of said compound is administered, said desired therapeutic effect being selected from the group consisting of (1) an alteration in the rate of fluid transport in the gastrointestinal tract of said mammal; (2) a reduction in the intraocular pressure in at least one eye of said mammal; and (3) an increase in the renal fluid in at least one kidney of said mammal, said compound being selected from the group consisting of those having the formula

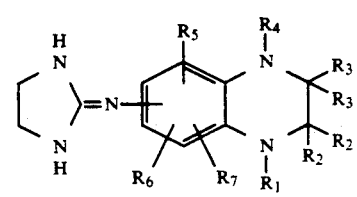

pharmaceutically acceptable acid addition sales thereof and mixtures thereof, wherein $R_1$ and $R_4$ are independently selected from the group consisting of H and alkyl radicals having 1 to 4 carbon atoms; the $R_2$s are each H or alkyl radicals having 1 to 4 carbon atoms or are, together, oxo; the $R_3$s are each H or alkyl radicals having 1 to 4 carbon atoms or are, together, oxo, provided that said $R_2$s or said $R_3$s are alkyl radicals; the 2-imidazolin-2-ylamino group may be in any of the 5-, 6-, 7- or 8- positions of the quinoxaline nucleus; and $R_5$, $R_6$ and $R_7$ each is located in one of the remaining 5-, 6-, 7- or 8- positions of the quinoxaline nucleus and is independently selected from the group consisting of Cl, Br, H and alkyl radicals having 1 to 3 carbon atoms; and a carrier component combined with said compound in an amount effective to facilitate the administration of said amount of said compound to said mammal.

20. A method of treating a mammal comprising administering to a mammal, in an amount sufficient to provide a reduction in the intraocular pressure in at least one eye of said mammal, a compound selected from the group consisting of those having the formula

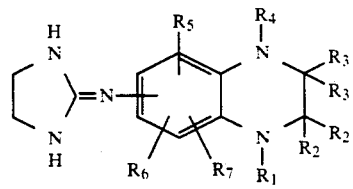

pharmaceutically acceptable acid addition sales thereof and mixtures thereof, wherein $R_1$ and $R_4$ are independently selected from the group consisting of H and alkyl radicals having 1 to 4 carbon atoms; the $R_2$s are each H or alkyl radicals having 1 to 4 carbon atoms or are, together, oxo; the $R_3$s are each H or alkyl radicals having 1 to 4 carbon atoms or are, together, oxo, provided that said $R_2$s or said $R_3$s are alkyl radicals; the 2-imidazolin-2-ylamino group may be in any of the 5-, 6, 7- or 8- positions of the quinoxaline nucleus; and $R_5$, $R_6$ and $R_7$ each is located in one of the remaining 5-, 6-, 7- or 8- positions of the quinoxaline nucleus and is independently selected from the group consisting of Cl, Br, H and alkyl radicals having 1 to 3 carbon atoms.

21. The method of claim 20 wherein the 2-imidazolin-2-ylamino group is in the 6- position of the quinoxaline nucleus, $R_5$ in the 5- position of the quinoxaline nucleus and is selected from the group consisting of Cl, Br and alkyl radicals containing 1 to 3 atoms, and $R_6$ and $R_7$ are both H.

22. The method of claim 20 wherein said $R_2$s or said $R_3$s are methyl radicals.

23. The method of claim 22 wherein $R_5$ is Br.

24. The method of claim 20 wherein said formula is:

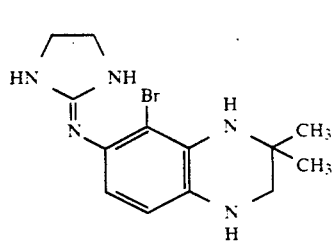

25. The method of claim 20 wherein said formula is:

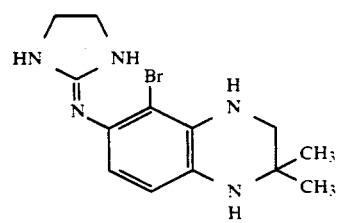

26. The method of claim 20 wherein said formula is:

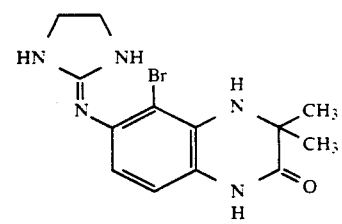

27. The method of claim 20 wherein said formula is:

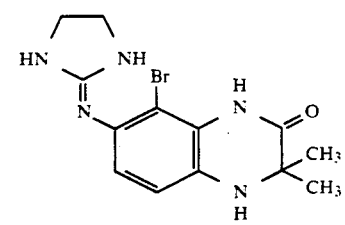

28. A method for reducing or maintaining the intraocular pressure in a mammalian eye comprising administering to a mammalian eye an effective amount to reduce or maintain the intraocular pressure in the mammalian eye of a compound selected from the group consisting of those having the formula

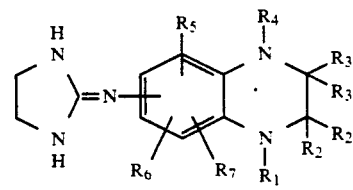

pharmaceutically acceptable acid addition salts thereof and mixtures thereof, wherein $R_1$ and $R_4$ are independently selected from the group consisting of H and alkyl radicals having 1 to 4 carbon atoms; the $R_2$s are each H or alkyl radicals having 1 to 4 carbon atoms or are, together, oxo; the $R_3$s are each H or alkyl radicals having 1 to 4 carbon atoms or are, together, oxo, provided that one of said $R_2$s and said $R_3$s are alkyl radicals; the 2-imidazolin-2-ylamino group may be in any of the 5-, 6-, 7- or 8- positions of the quinoxaline nucleus; and $R_5$ $R_6$ and $R_7$ each is located in one of the remaining 5-, 6-, 7- or 8- positions of the quinoxaline nucleus and is independently selected from the group consisting of Cl, Br, H and alkyl radicals having 1 to 3 carbon atoms.

29. The method of claim 28 wherein said compound is administered directly to the mammalian eye.

30. The method of claim 28 wherein said compound is administered directly to the mammalian eye in an amount effective to reduce the intraocular pressure in the mammalian eye.

31. The method of claim 28 wherein the 2-imidazolin-2-ylamino group is in the 6- position of the quinoxaline nucleus, $R_5$ in the 5- position of the quinoxaline nucleus and is selected from the group consisting of Cl, Br and alkyl radicals having 1 to 3 atoms, and $R_6$ and $R_7$ are both H.

32. The method of claim 28 wherein said $R_2$s or $R_3$s are methyl radicals.

33. The method of claim 32 wherein $R_5$ is Br.

34. The method of claim 28 wherein said formula is:

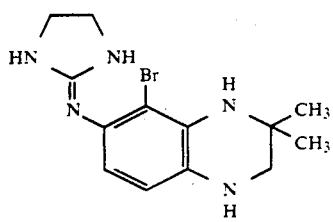

35. The method of claim 28 wherein said formula is:

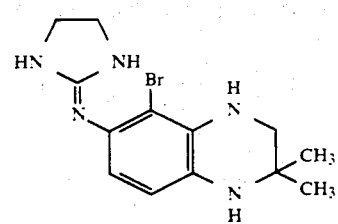

36. The method of claim 28 wherein said formula is:

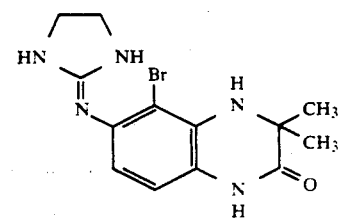

37. The method of claim 28 wherein said formula is:

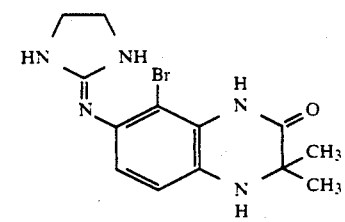

* * * * *

UNITED STATES PATENT AND TRADEMARK OFFICE
CERTIFICATE OF CORRECTION

PATENT NO. : 5,112,822
DATED : May 12, 1992
INVENTOR(S) : Charles Gluchowski

It is certified that error appears in the above—identified patent and that said Letters Patent is hereby corrected as shown below:

Column 1, line 37, change "triflucromethyl" to -- trifluoromethyl -- .

Column 4, line 7, change "-0.25" to -- _0.25 -- .

Column 7, line 22, change "quinonxalinone" to -- quinoxalinone -- .

Column 7, line 26, change "H2" to -- $H_2$ -- .

Column 7, line 54, before "cooled" delete --< -- .

Column 7, line 67, change "$^\circ$C" to -- $0^\circ C$ -- .

Column 8, line 21, change "quinoxali none" to -- quinoxalinone -- .

Column 8, line 35, change "quinonxalinone" to -- quinoxalinone -- .

Column 8, line 44, change "dimethyl" to -- dimethyl- -- .

Column 8, line 50, change "quinoxaline" to -- quinoxalinone -- .

Column 9, line 29, change "KH2 PO4" to -- $KH_2 PO_4$ -- .

Column 11, line 47, after the first occurrence of "said" delete "said".

Column 12, line 57, after "fluid" insert -- flow -- .

Column 13, line 40, change "sales" to -- salts -- .

UNITED STATES PATENT AND TRADEMARK OFFICE
CERTIFICATE OF CORRECTION

PATENT NO. : 5,112,822
DATED : May 12, 1992
INVENTOR(S) : Charles Gluchowski

It is certified that error appears in the above—identified patent and that said Letters Patent is hereby corrected as shown below:

Column 15, line 21, change "$R_5$ in" to -- $R_5$ is in -- .

Signed and Sealed this

Twenty-eighth Day of September, 1993

*Attest:*

BRUCE LEHMAN

*Attesting Officer*  *Commissioner of Patents and Trademarks*